United States Patent [19]

Kiesewetter et al.

[11] Patent Number: 4,519,239
[45] Date of Patent: May 28, 1985

[54] APPARATUS FOR DETERMINING THE FLOW SHEAR STRESS OF SUSPENSIONS IN PARTICULAR BLOOD

[75] Inventors: Holger Kiesewetter, Usch; Friedrich Jung, Aachen; Hartmut Radtke, Aachen; Reinhard Witt, Aachen, all of Fed. Rep. of Germany

[73] Assignee: Holger Kiesewetter, Homburg-Kirrberg, Fed. Rep. of Germany

[21] Appl. No.: 493,594

[22] Filed: May 11, 1983

[30] Foreign Application Priority Data

May 13, 1982 [DE] Fed. Rep. of Germany ....... 3218037

[51] Int. Cl.³ ............................................. G01N 11/04
[52] U.S. Cl. ............................................. 73/55; 73/56
[58] Field of Search .................. 73/53, 54, 55, 56; 356/39

[56] References Cited

U.S. PATENT DOCUMENTS 3,559,464 2/1971 Foust et al. ............................. 73/55
3,908,442 9/1975 Chmiel ................................... 73/55
4,143,541 3/1979 Ito et al. ................................. 73/55

OTHER PUBLICATIONS

J. J. Mills et al, A High Shear Rate, High Temperature Rheometer for Molten Glass. (Aug. 1970).
Neville, U.S. Defensive Publication, (Jul. 5, 1977).
Jean L. Leblance, Polymer Melt Flow Properties and Stress Relaxation Measurement with Slit Die Rheometer (1976).

Primary Examiner—Anthony V. Ciarlante
Assistant Examiner—Hezron E. Williams
Attorney, Agent, or Firm—Cushman, Darby & Cushman

[57] ABSTRACT

The invention concerns a measuring apparatus for checking and determining the flow shear stress of certain suspensions, principally blood, by a static or dynamic method and to thereby plot the viscosity of the suspension. The apparatus employs an internal measuring chamber comprised of a passage arrangement to simulate the natural microcirculation area wherein a network of capillary passages diverge from a main passage, with at least two of the capillary passages of different lengths, with a length ratio that can range from 3:1 to 15:1, with those capillaries connected to a source of variable pressure and extending past a detector unit.

15 Claims, 4 Drawing Figures

ND: 4,519,239

APPARATUS FOR DETERMINING THE FLOW SHEAR STRESS OF SUSPENSIONS IN PARTICULAR BLOOD

The invention relates to an apparatus for determining the flow shear stress of suspensions, in particular blood, comprising a means having a network of capillary passages.

As it is known, blood can be taken as an independent mobile organ which consists of various cells which are suspended in a fluid phase, namely the plasma. The main function of blood is to convey oxygen and nutrients to the parenchyme cells and to carry away carbon dioxide and metabolics. In addition, blood performs a large number of other functions including heat distribution, the vehicle function for hormones, defense against morbific agents and substances foreign to the body, etc. These functions may be combined under the term homeostasis, the maintenance of a dynamic (flow) equilibrium.

To ensure homeostasis in all organs a minimum flow of blood is necessary in the vessels in which the material exchange takes place, i.e. in the microcirculation areas. The flow is normally controlled primarily by variation of the vascular diameter of the arterioles and to a lesser extent also by variation of the driving pressure, by regulation of the heart ejection capacity. The effectiveness of this regulation is derived from the Hagen-Poiseuille law, according to which the flow rate is dependent on the forth power of the radius.

However, in conditions in which these possibilities of regulation are fully exhausted, for instance with pronounced vascular sclerosis or behind vascular stenosis at which a broadening of the arterioles has occurred, a further factor becomes predominant, that is the internal friction or viscosity of the blood. The blood viscosity is not a constant for a controlled temperature but depends greatly on the shear forces in the blood vessels. With a slow flow, i.e. small shear forces, the viscosity is greatly increased and can thus become a limiting factor for the circulation. It is agreed that tightly packed cell suspensions with hematocrit values above 0.7 under small shear stresses can exhibit the behaviour of a solid body, whilst the same suspensions under a high shear stress (increased flow rates) exhibit an astonishingly high fluidity.

However, it is not established whether normal full blood with a hematocrit value of 0.45 has a flow point, i.e. under small external stress behaves like a solid body and when a mechanical threshold is exceeded by increasing the shear stress behaves like a fluid.

A flow point exists if under a finite driving pressure the investigated fluid does not flow. In other words, below a limit flow shear stress $\tau_y$ the fluid has an infinitely high viscosity and thus exhibits solid body behaviour. To exactly define this flow shear stress requires the exact definition of the term "flow standstill". As is known the flow point of the blood extrapolated from macroviscosimetric measurements depends on the fibrinogen concentration and thus on the erythrocyte aggregation, but in addition is also greatly dependent on the hematocrit value and, as discovered only recently, on the erythrocyte deformability.

Now, the phenomenon of the "flow point" of blood is gaining interest in the diagnosis and therapy supervision of patients with flow anomalies because it is now possible therapeutically to alter in vivo the fibrinogen content and the hematocrit value and thus two determinants of the flow point measurable in vitro.

In recent years a great number of methods have been developed for measuring the flow shear stress. It is usual to divide the various determination methods of the flow shear stress into static and dynamic methods.

In the static methods the fluid investigated is at first at rest ($\gamma = 0$). The shear stress is thereafter increased until the fluid begins to flow.

In the dynamic methods the fluid is initially moving; the shear stress is then reduced until a standstill is reached.

It may be assumed that with constant hematocrit value with the static methods higher values are obtained for $\tau_y$ than with the dynamic. The reasons for this are:
 (a) The disaggregation requires higher shear stresses than the aggregation (overcoming the adhesive forces or adhesive friction).
 (b) The aggregates become larger in stasis and consolidate.
 (c) The functional hematocrit value, i.e. the hydrodynamic effective volume fraction of the erythrocytes, is higher in stasis because of the larger aggregates (inclusion of plasma in the aggregates, which cannot be sheared).

In particular, the dynamic measurement is made complicated because excessive sedimentation effects can occur and thus possibly even local hemoconcentration, which can lead to an increase in the flow shear stress. However, in this case in a strictly rheological sense it is no longer possible to refer to a flow shear stress because the latter is defined only for an unchanged composition of the suspension investigated. Because of the inevitable sedimentation of blood when using dynamic methods it is at the most possible to speak of a flow shear stress after hemoconcentration has taken place. Since these factors can play a very important part in circulation disturbances it is useful to abandon the usual strict definition of the flow point in general rheology.

For the quantification of the flow shear stress in the past balance, capillary and rotation viscosimeters and a sedimentation chamber have been used. The balance viscosimeter is described for example in Biorheology 6 (1969), pages 23–32, a capillary viscosimeter in Biorheology 5 (1968), pages 263–270, a rotation viscosimeter in Biorheology 7 (1970), pages 129–135, and a sedimentation chamber in NATURE 216 (1967), pages 1121–1123. Below the advantages and disadvantages of these methods will be briefly explained.

In the balance methods via a fine balance an immersion body of higher density is suspended in the fluid to be investigated. Acting thereon are gravity and buoyancy which are in static equilibrium. To deflect said body from the rest position a force must be applied with the aid of which any resilient resistance to the movement can be measured. The maximum force with which the fluid opposes a movement of the immersed body is the flow shear stress $F_y$. Conversely, in the dynamic system the immersed body is first in motion. After stopping the motion the flow shear stress can be determined with the aid of the equilibrium condition and said flow shear stress can be calculated for a known surface of the body A. However, this method gives extremely fluctuating results when applied to blood. Thus, carefully taken and completely reproduced results fluctuate by an average of 40% but in some cases by more than 400%.

In the static sedimentation method an upwardly conically tapering glass tube is used whose internal diameter is between 2 and 0.08 mm. The glass tube is filled with blood and stood upright with the smaller diameter at the top for about 10 minutes. Below a predetermined tube diameter $d_y$ a column of erythrocyte sediment as aggregates. Above this diameter the aggregated erythrocyte column remains at rest in the top of the glass cone. For this diameter, neglecting the cone angle, a balance of forces is drawn up from which the flow shear stress can then be determined. However, with this method only the shear stress is determined which leads to the tearing away of aggregates within a sedimentated erythrocyte column and consequently this method cannot determine the flow point of the blood but only that of the aggregates.

A further already mentioned method is the flow point determination with rotation viscosimeters. These rotation viscosimeters developed in the technical sciences with varying geometry have been used for a long time also for hemorheological investigations. Common to the usual apparatuses is that various mostly constant rotation speeds are prescribed and thus finite shear degrees ($\gamma = 10^{-3} - 10^2 1/s$). By the fluid torques and thus shear stresses are transmitted to a sensor.

According to the Casson equation introduced into hemorheological literature, with which the flow behaviour can be described over a wide shear degree range by the relationship $$\sqrt{\tau} = k_1 + k_2 \sqrt{\gamma}$$

the flow curve was extrapolated in various cases to $\gamma = 0$, whereby $\tau_y = k_1^2$ (with shear degrees of $10^{-2}$ to $50\ s^{-1}$) was calculated. This method has frequently been critized but is nevertheless often employed in the literature.

The basic difficulty in flow shear stress measurements hitherto resides in that rotation viscosimeters are used with which a finite shear degree, i.e. at the same time a flow, is prescribed and any flow point existing cannot therefore be covered by the measuring techniques but must be extrapolated in various ways.

An improvement in the measuring method with rotation viscosimeters is the DEER viscosimeter in which in contrast to most other hitherto used rotation viscosimeters the torque and thus the shear stress (and the pressure) is prescribed and thus the shear degree is defined. The latter may also be zero so that the flow shear stress $\tau_y$ can be measured directly in a macroscopic range. Such a measurement can thus provide only information for this range and at most can be used for extrapolation for the microcirculation range.

A further possibility of determining the flow shear stress is the investigation of the dependence of the velocity v on the pressure gradient $\Delta p$ in capillary viscosimeters. An extrapolation may be made of this $\Delta p$-v diagram after the conversion of the data the $\gamma - \tau$ diagram for $v = 0$ or $\gamma = 0$. Capillaries are used with a diameter of 0.05 to 1 mm and a length of up to 8 m. A main disadvantage of this method is that most measurements were made without optical observation of the erythrocyte flow. As the observations of Devendran, PROC. ASME 73-WA/BIO 35 (1973), pages 1–4, show, with the capillary viscosimeters no flow point can be determined because a flow standstill of the erythrocytes never occurs.

Thus, the question whether human blood has a finite flow shear stress has still not been solved. The problem underlying the invention is therefore to provide an apparatus of the type mentioned at the beginning with which the flow shear stress of suspensions, in particular blood, can be simulated in regions having a network of capillary passages.

This problem is solved by the features of the characterizing clause of claim 1.

The invention now provides a measuring apparatus with which it is possible in simple and reproducible manner to determine the flow shear stress of blood by the static or dynamic method and if necessary to plot the flow curve of the blood in particular in the region of small shear stresses ($\tau < 500$ mPa).

By evaluation of the flow curve it is possible to observe and quantitatively determine the non-Newtonian behaviour of blood. Thus, for example, the behaviour of blood depends not only on the temperature but also on the shear forces acting. The reasons are the behaviour of the suspended or emulsified particles, i.e., their deformation and orientation, and their interactions with each other, thus above all the aggregation. With ideal Newtonian fluids the shear rate increases linearly with increasing shear stress, i.e. they have a constant viscosity which is formed as quotient of the shear stress and shear rate. If however with full blood the shear stress is plotted against the shear rate, it is found that the slope of the curve is not constant. This slope is referred to as "apparent" viscosity $\eta_{app}$.

Now, for small shear stresses the behaviour of blood exhibits so-called dilatance, i.e. the apparent viscosity increases with increasing shear stress, and for higher shear stresses a structural viscous behaviour. With the erythrocyte-stasis measuring apparatus (ESM) according to the invention the dilatance of blood, a quantity which also has rheological significance, can be determined from the flow curve found for small shear stresses and thus quantitatively measured.

A further property of blood, i.e. the increase with time of the apparent viscosity (rheopexy) can be simply observed optically with the viscosimeter according to the invention and possibly quantitatively measured.

One of the essential parts of the ESM according to the invention is the measuring means which is preferably in the form of a measuring chamber. In this measuring chamber the natural microcirculation area is simulated by an artificial in vitro network present in simplified form. This artificial network comprises essentially at least two passages which advantageously branch off from a supply passage at any desired angle. An essential point in this arrangement is that the two capillary passages have different length. The different length of the passages is intended to take account of the in vivo behaviour of blood in microcirculation areas with different hydrodynamic resistance. As is known, blood exhibits the stasis phenomenon in which although it flows in relatively short capillary passages it does not flow in long capillary passages preferably connected in parallel thereto.

With the present measuring chamber this behaviour of blood in microcirculation areas can be successfully simulated. Thus, it is possible with the apparatus according to the invention to establish that blood of a predetermined composition will flow in short passages under certain shear stresses but will remain in the stationary state in long passages. The parameter at which the blood also begins to flow in the long passages is a criterion for the flowability of the blood in the less perfused microcirculation.

The invention will be explained in detail with reference to the following description of embodiments with the aid of the drawings, wherein.

Figure 1:
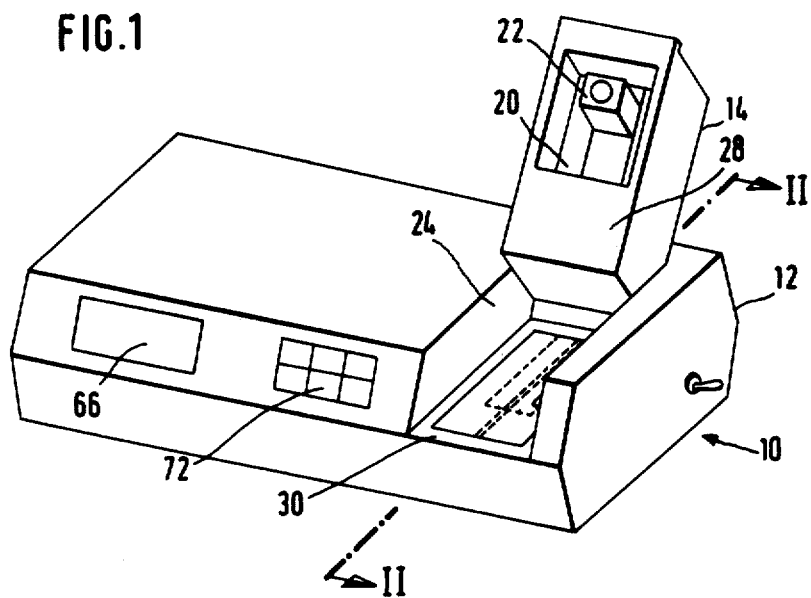
FIG. 1 is a perspective view of the apparatus according to the invention.

In FIG. 1 the apparatus according to the invention is designated by 10. This apparatus 10 comprises essentially a housing 12 having a pivotal cover 14. Said cover 14 can be swung about the horizontal axis 16 and is so designed that in the opened condition it can bear against the inclined face 18 provided in the housing 12 and be supported thereon.

The cover 14 comprises at its lower side a recess 20 in which a detector unit 22 is provided which according to a preferred embodiment is horizontally displaceable.

The cover 14 itself closes flush with an opening 24 provided in the housing 12 and in the closed condition actuates an electrical contact 26 which is provided on the inclined surface 18 and which renders the apparatus 10 ready for operation.

The opening 24 comprises a horizontal support surface 30 for the lower side 28 of the cover 14, said surface 30 comprising a substantially rectangular cutout 32 for accommodating the measuring chamber 34. As apparent from FIG. 1 the measuring chamber 34 occupies substantially the entire cutout 32 and forms together with the support surface 30 a uniform surface.

Beneath the measuring chamber 34 adjoining the cutout 32 is a further recess 36 within which a further detector unit 38 is disposed, which is either fixedly connected to the detector unit 22 or is synchronized therewith. The detector unit 38, like the detector unit 22, is horizontally displaceable as indicated by the arrow in FIG. 2 within the recesses 36 and 20, respectively, which are substantially in vertical alignment, said detectors being in the immediate vicinity of the upper side 40 and the lower side 42 of the measuring chamber 34.

Figure 3:
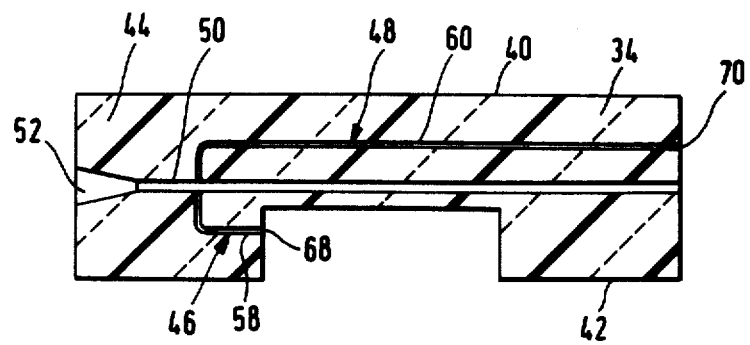
FIG. 3 is a plan view of a measuring chamber which is provided in the apparatus according to FIGS. 1 and 2 and FIG. 4 is a longitudinal section through a further embodiment of a measuring chamber.
Figure 4:
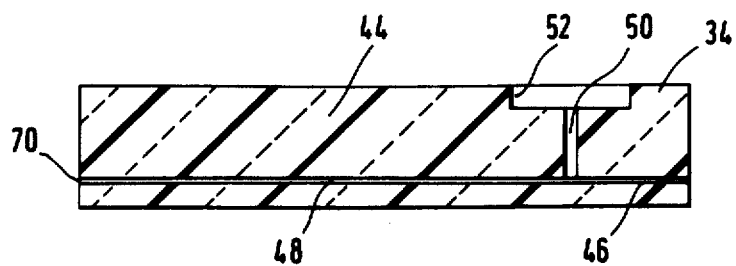

According to the embodiments shown in FIGS. 3 and 4 the measuring chamber 34 consists essentially of the solid body 44 into which preferably two passages 46 and 48 are worked. Said passages 46 and 48 are essentially of a capillary nature, i.e. they have a diameter of 15-1000, in particular 30-150 μm.

The form of the cross-section of these passages 46 and 48 is essentially not critical and preferably should be oval to circular.

The ratio of the length $L_1$ of the long passage 48 and the length $L_k$ of the short passage 46 should be in a range of 3:1-15:1, preferably 6:1-10:1, in particular 7:1.

In the embodiments shown in FIGS. 3 and 4 the passages 46 and 48 branch off from a main passage 50 via which the the fluid to be investigated, in particular blood, is supplied. Said passage 50 comprises a supply opening 52 which is widened with respect to the cross-section of the main passage 50. Said supply opening 52 may either have the conical form shown in FIG. 3 or the cylindrical form shown in FIG. 4, the latter being concentric with the main passage 50.

Said supply opening 52 is connected to a supply means 54 which is provided in the housing 12 and through which the fluid to be investigated, in particular blood, is supplied to the measuring chamber 34 from a reservoir which is not shown.

Figure 2:
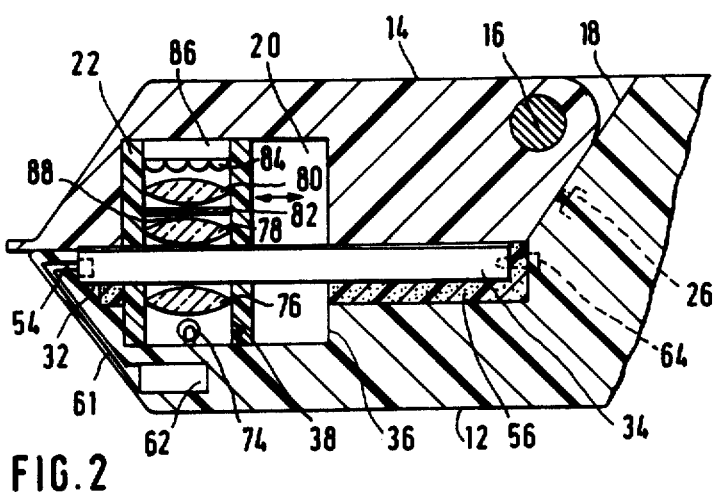
FIG. 2 is an enlarged sectional view along the line II—II through the apparatus of FIG. 1, but with the latter closed.

According to the embodiment shown in FIG. 2 the supply opening 52 on insertion of the measuring chamber 34 is first brought into connection with the supply means 54. Thereafter, the end of the measuring chamber 34 opposite the supply opening is inserted into the cutout 32 and the resilient member 56 provided in the cutout 32 and consisting preferably of a foamed plastic ensures a pressure-tight fit between the supply means 54 and the supply opening 52.

The diameter of the main passage 50 is advantageously greater than the diameter of the passage 46 and 48 and is 30-2000, in particular 60-300 μm. Its form corresponds to the form described above for the passages 46 and 48.

The passages 46 and 48 can branch off the main passage 50 at various angles. Preferably, they branch off substantially at a right-angle from the main passage 50 as shown in FIGS. 3 and 4.

According to a first embodiment illustrated in FIG. 3 the passages 46 and 48 each branch off again at a right-angle and form a substantially U-shape. The branches 58 and 60 extend substantially parallel.

In a second embodiment illustrated in FIG. 4 there is no such second branch so that the passages 46 and 48 have essentially a common longitudinal axis.

The production of a branch between the main passage 50 on the one hand and the side passages 46 and 48 on the other was hitherto an unsolved problem and is solved by the method outlined below.

The network is produced substantially by casting with a pourable substantially transparent plastic, for example with polyester. Such a pourable blood-compatible plastic is used with the usual addition of accelerating and hardening agents and during curing must shrink only slightly. Furthermore, it must be ensured that air inclusions formed in mixing and casting pass in the form of bubbles before the curing to the surface and can thus be removed.

Such a plastic is cast into a correspondingly prepared mould corresponding substantially to the form of the measuring chamber 34.

Capillary passages are worked into the solid body 44 in that unstretched filaments whose cross-section and diameter correspond substantially to the required dimensions of the passages 46 and 48 are disposed in the form in the desired arrangement and thereafter the castable composition introduced. Polyamide may for example be used as material for such filaments. Preferably, monofilament nylon threads are used which are advantageously provided with a corresponding separating agent, for example PTFE.

To obtain a corresponding branching with the main filament serving as main passage 50 said filament is bored with the filament used for making the passages 46 and 48, which is preferably done under a microscope with a correspondingly dimensioned neadle into which the filament used for making the passages 46 and 48 is inserted. Such a branching is located in the manner explained above in the mould so that the desired geometry ($L_1/L_k$) results. These filaments are led out of the mould and thus project from the hardened plastic block forming the solid body 44.

Since unstretched filaments are used they may be removed by stretching, i.e. pulling, from the hardened plastic block, leaving the capillary passages 46, 48 and 50.

This production manner makes it possible for the first time to produce in vitro networks with genuine branches in which the microcirculation region in which the blood is led can be simulated.

In principle, apart from the arrangements of the passages 46, 48 and 50 shown in FIGS. 3 and 4 geometrical arrangements of any desired complicity may of course be made.

Thus, in a specific embodiment it is perfectly conceivable for the short passage and the long passage each to have a common entry and exit opening. The short passage is substantially in stretched form whilst the long passage is led in any desired convolutions or geometrical arrangements within the solid body 44. However, because of the measuring technique it is preferable for such convolutions to lie substantially in the horizontal plane or the measuring plane.

According to this embodiment the entry and exit openings may have a supply opening corresponding substantially to the supply opening 54. And exit opening having the same form can of course also be provided. Since in this embodiment a main passage having a corresponding branching is not provided the supply opening can merge additionally into a short main passage which merges directly into the short and long side passages.

Instead of the filaments described above for making the passages 46, 48 and 50 industrially prepared hollow filaments may be used, as for example employed in dialysis. Such hollow filaments have the aforementioned dimensions for the diameter and the form of the passages. If hydrophilic hollow fibres are used, for example from cellulose derivatives, such a filament must of course be completely cast into a plastic matrix to prevent an expulsion of plasma from the micropores. Such an expulsion can be prevented with hollow filaments of a hydrophobic material, for example polypropylene, so that a complete casting out of the solid body 44 may be superfluous. It has however been found advantageous for the passages 46 and 48 to be located in a matrix, for example the plastic matrix, in order to minimize problems in the measurement made by optical means.

Apart from the production of filament intersections with the aid of a needle other methods may of course be used, such as drilling, piercing or electron-ray techniques. Since however particular requirements must be made of the pore geometry and the reproducibility of the pore diameters, in particular the nuclear track technique is suitable. In this method, instead of the desired hole a single high-energy heavy ion is shot through and the "radical" track formed along the particle path etched out in a second production step to the desired diameter.

By corresponding dimensioning of such a particle it can be achieved that the result is not a through-bore but only a blind hole as shown for example in FIG. 4.

The measuring chamber 34 is preferably made as a so-called once-only part or disposable part, i.e. after use it is removed from the apparatus 10 and thrown away. Obviously, the blood reservoir not shown can be integrated into the measuring chamber 34 as well, i.e. can be disposed for example directly in front of the supply opening 52 and the supply means 54.

The supply means 54 is connected via a conduit 61 to the pressure generator 62 which produces the pressure necessary for filling the measuring chamber 34 and carrying out the measurement. Thus, the suspension is first introduced into the network at a high pressure of about $1 \text{ mH}_2\text{O} = 10^4$ Pa. Thereafter, said pressure generator 62 can reduce the pressue to O; a pressure increase in steps of about 2.5 Pa and above can be carried out.

If the embodiment shown in FIG. 3 is filled with blood the main passage 50 must of course be closed after the filling and this can be done by the plug 64 which can be provided in the measuring chamber 34. This plug may for example be an electromagnetic closure means.

For the measurement, a maximum of 2 ml venous full blood is required with a hematocrit content >0.4 in the anticoagulated state. Prior to the measurement this blood is introduced into the measuring chamber as a whole, i.e. via the main passage 50 into the side passages 46 and 48. The filling can be carried out either outside the apparatus or within the apparatus. Preferably, for simplicity the measuring chamber 34 is filled outside the apparatus and then inserted into the cutout 32. As explained above, the measuring operation is started with the closure of the cover 14 and proceeds substantially automatically. The measuring result obtained is indicated via the display 66 which is disposed in the housing 12.

Before the start of the actual measurement a pressure compensation is carried out between the short and the long passage 46 and 48, such that the pressure difference acting via the passages is compensated to zero. This is done by varying the pressure applied. Zero pressure is defined as the pressure which for a predetermined minimum time, for example one minute, effects no flow in the short passage. After this zero compensation the determination of the flow shear stress can begin. For this purpose the pressure must be determined at which the erythrocytes in the long passage 48 begin to flow or are just about to flow. To determine this so-called static limit pressure differential $\Delta p_{ys}$ the pressure is increased in discrete steps, for example 1-10, in particular 2.5 Pa, until a flow can be observed in the long passage. Between each pressure increase there is an adjustment time of 0.1-5, in particular about one minute. A flow is defined as any cell displacement in the long passage 48 which is faster than 0.1-10, especially 0.5 $\mu$m min.$^{-1}$.

The pressure can be produced in the pressure generator 62 both pneumatically and, which is preferable, hydrodynamically. For this purpose, in the measuring chamber advantageously a fluid reservoir can be provided which serves to apply the pressure. Furthermore, the pressure generator can be disposed also at the outlet openings 68 and 70 of the short and long passages 46 and 48, respectively and of course a correspondingly dimensioned vacuum is applied with the aforementioned pressure steps in the opposite direction.

As soon as a visible cell displacement is detected in the long passage 46 by the detector unit 22 and 38 described in detail below the flow point is exceeded and the test is automatically evaluated. For this purpose, the flow shear stress $\tau_y$ is calculated as rheological quantity from the last pressure differential which did not produce any flow.

Since the value depends however greatly on the hematocrit value of the sample it should be corrected for comparison purposes to a reference hematocrit value of for example 0.45. This hematocrit value can either be introduced into the apparatus 10 via a key board 72 or preferably itself determined parallel to the measurement in the apparatus, the key board then being dispensed with. With the aid of the actually obtained hematocrit value a corrected flow shear stress $\tau_{ykorr45}$ is calculated and shown on the display 66.

Since the velocity measurement necessary for the zero point determination and the flow point measurement cannot be realized with conventional measuring methods because of the extremely small velocities (0.5 $\mu$m min$^{-1}$) a detector system 22,38 has been developed which permits a decision on a flow or stationary state even for the smallest velocities.

The measuring method used employs the effect that the intensity of the transmitted light passing through a capillary varies at least locally during the movement or the transition from the stasis to the flow and vice versa. The detector unit 38 comprises a light source 74 which is followed by a magnification optical system which includes three lenses 76, 78 and 80 which are disposed in the detector units 22 and 38. Between the lenses 78 and 80 is a diaphragm 82 which defines a local cutout of definite size and form from the light. The diaphragm may comprise a circular or a rectangular opening. The diameter of the circular opening is in the region of 5–50, especially 10–30 $\mu$m, whereas when a rectangular opening is used the width of the gap is 5–50, especially 10–30 $\mu$m, and its length 5–1000, especially 10–150 $\mu$m. The light passing the diaphragm 82 is expanded with the lens 80 and projected onto the light detector 84. The latter may consist of a single light sensor or preferably of an n x m matrix of light sensors, for example semiconductor sensors. The light detector is followed by an electronic amplifying unit 86 which detects the smallest changes in the transmitted light and notifies the electronic evaluation unit, not illustrated, of the state of the stasis or flow. Since the change of the transmitted light is greatest at points of local transmission extremes, to increase its sensitivity the entire optical evaluation unit may possibly be moved manually or with the aid of a stepping motor until such an extreme value is found. Separate optical evaluation units may be provided for each of the short and long passages 46 and 48. However, if the entire unit is movable a single unit is sufficient for both passages. The positioning then necessary takes place via the electronics incorporated. Instead of a moving electronics system it is of course possible to provide a plurality of fixed measuring points on the detector unit 22. For this purpose, it is only necessary for the diaphragm 82 to have a plurality of openings 88 through each of which a light beam must pass which has passed through the short or long passage 46 or 48 respectively. Associated with such openings 88 in each case is a light detector 84 which is connected separately to the evaluation unit.

With the geometry explained it is also possible by variation of the intersection angle and the diameter of the side passages 46 and 48 to quantify a parameter important to blood rheology and hitherto not quantifiable, i.e. the hematocrit distribution in parallel vessels. Thus, for example, in the passage 46 and 48 electrodes may be provided for measuring the conductivity of the blood column disposed in the passages 46 and 48. The hematocrit value can then be concluded for the conductivity obtained. Such a measuring arrangement is for example described in German application P 32 02 067.8, to the disclosure of which express reference is made.

We claim:

1. Apparatus for determining the flow shear stress of suspensions, in particular blood, comprising a means having a main passage therein and a network of capillary passages, said capillary passages diverging from the main passage at an angle characterized by at least two capillary passages of which the ratio of the length $L_l$ of the long passage and the length $L_k$ of the short passage lies in a range of 3:1 to 15:1 and which are connected to a means for producing a variable pressure differential, and by a detector system with which the flowing of the fluid can be detected.

2. Apparatus according to claim 1, characterized in that the ratio is about 7:1.

3. Apparatus according to claim 1, characterized in that the internal diameter of the passages (46,48) is about 15–1000 $\mu$m.

4. Apparatus according to claim 1, characterized in that the passages (46,48) are connected at their entry opening to a main passage (50).

5. Apparatus according to claim 4, characterized in that the passages (46,48) are connected in U-form to the main passage (50).

6. Apparatus as in claim 1 wherein said variable pressure means comprises a hydrodynamic pressure generator.

7. Apparatus according to claim 1, characterized in that the means for producing a variable pressure differential in the passages (46,48) is a pneumatic pressure generator (62).

8. Apparatus according to claim 1, characterized in that the detector system (22,38) comprises a light source (74), a magnifying optical system (76,78,80), a diaphragm (82) and at least one light detector (84).

9. Apparatus according to claim 8, characterized in that the detector system (22,38) comprises light sensors corresponding to a plurality of fixed measuring points.

10. Apparatus for determining the flow shear stress of suspensions, in particular blood, comprising a means having a network of capillary passages, at least two of said capillary passages having a length ratio between the length $L_l$ of the long passage and the length $L_k$ of the short passage ranging from 3:1 to 15:1, said network of capillary passages being connected to a means for producing a variable pressure differential, and a detector system with which the flowing of the fluid can be detected, wherein said passages are connected at their entry opening to a main passage and wherein the passages are provided in a solid, cast body of a substantially transparent plastic.

11. Apparatus for determining the flow shear stress of suspensions, in particular blood, comprising measuring chamber means having a network of capillary passages, characterized by at least two capillary passages having a length ratio between the length $L_l$ of the long passage and the length $L_k$ of the short passage ranging from 3:1 to 15:1 and which are connected to a means for producing a variable pressure differential, and by a detector system with which the flowing of the fluid can be detected, wherein said passages are connected at their entry opening to a main passage and wherein said measuring chamber means is comprised of a solid body and wherein hollow filaments of a hydrophobic material are provided in said solid body and comprise said passages.

12. Apparatus for determining the flow shear stress of suspensions, in particular blood, comprising a means having a network of capillary passages, characterized by at least two capillary passages of which the ratio of the length $L_l$ of the long passage and the length $L_k$ of the short passage lies in a range of 3:1 to 15:1 and which are connected to a means for producing a variable pressure differential, and by a detector system with which the flowing of the fluid can be detected and wherein said means having a network of capillary passages further includes a main passage, with said capillary passages and said main passage comprising a measuring chamber which is provided within the detector system.

13. Apparatus for determining the flow shear stress of suspensions, in particular blood, comprising a means having a network of capillary passages, characterized by at least two capillary passages of which the ratio of the length $L_l$ of the long passage and the length $L_k$ of the short passage lies in a range of 3:1 to 15:1 and which are connected to a means for producing a variable pressure differential, and by a detector system with which the flowing of the fluid can be detected wherein at least one of the said capillary passages includes electrodes for determining the conductivity of the suspension disposed in that respective passage.

14. Apparatus for determining the flow shear stress of suspensions, in particular blood, including a measuring chamber formed from a substantially transparent material, said chamber including a main passage, at least a first capillary passage for the suspension material connected to a pressure generator by way of said main passage, said apparatus further including a movable optical detector system for observing the supension material in said at least first capillary passage, at least a second capillary passage, said at least first and second capillary passages being comprised of different lengths and arranged rectangularly to said main passage.

15. Apparatus according to claim 14, wherein the ratio of the length $L_l$ of the longer of said capillary passages and the length $L_k$ of the shorter of said capillary passages lies in a range of 3:1 to 15:1.

* * * * *